US006585645B2

(12) United States Patent
Hutchinson (10) Patent No.: US 6,585,645 B2
(45) Date of Patent: Jul. 1, 2003

(54) SYSTEM FOR AND METHOD OF ESTABLISHING MONITORING ALARM LIMITS BASED ON PHYSIOLOGICAL VARIABLES

(75) Inventor: George M. Hutchinson, Brookfield, WI (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 232 days.

(21) Appl. No.: 09/858,808

(22) Filed: May 16, 2001

(65) Prior Publication Data

US 2002/0177755 A1 Nov. 28, 2002

(51) Int. Cl.[7] .................................................. A61B 5/02
(52) U.S. Cl. ...................... 600/300; 600/301; 600/481; 600/508; 600/529; 340/573.1
(58) Field of Search ............................... 600/300, 301, 600/529–539, 481–486, 500, 508; 340/573.1

(56) References Cited

U.S. PATENT DOCUMENTS

| 5,438,983 A | * | 8/1995 | Falcone ...................... 600/301 |
| 5,609,156 A | * | 3/1997 | Keith et al. .................. 600/483 |
| 5,724,983 A | * | 3/1998 | Selker et al. ................ 600/301 |
| 6,241,661 B1 | * | 6/2001 | Schluess et al. ............ 600/300 |
| 6,506,153 B1 | * | 1/2003 | Littek et al. ................ 600/301 |

FOREIGN PATENT DOCUMENTS

| DE | 2527475 | * 12/1976 |

OTHER PUBLICATIONS

Richard L. Keenan, M.D., "Anesthetic Disasters And Their Prevention," Annual Meeting of the American Society of Anesthesiologists, presented Oct. 14–18, 1989.

Koski et al., "Clinicians' Opinions on Alarm Limits and Urgency of Therapeutic Responses," International Journal of Clinical Monitoring and Computing 12: 85–88, 1995.

Lunn et al., "Perioperative Mortality: Lessons from the Confidential Enquiry into Perioperative Deaths in Three NHS Regions," The Lancet, v. 330, No. 8572, Dec. 12, 1987, pp. 1384–1386.

John W. R. McIntyre, "Ergonomics: Anaesthetists' use of Auditory Alarms in the Operating Room," International Journal of Clinical Monitoring and Computing 2: 47–55, 1985.

Annejet P. Meiljer, "The Anesthesiologists's Work in the Operating Room," chapter 2 of "Automation in Anesthesia A Relief?", Springer–Verlag, 1987, pp. 10–29.

Meredith et al., "Are There too Many Alarms in the Intensive Care Unit? An Overview of the Problems," Journal of Advanced Nursing, 1995, 21, pp. 15–20.

Mylrea, et al., "Integration of Monitoring for Intelligent Alarms in Anesthesia: Neural Networks—Can They Help?," Journal of Clinical Monitoring, vol. 9, No. 1. Jan. 1993, pp. 32–37.

Tsien et al., "Poor Prognosis for Existing Monitors in the Intensive Care Unit," Crit Care Med 1997, vol. 25, No. 4, pp. 614–619.

J.H.M. van Oostrom, "A System for Automatic Alarm Limit Setting in Anesthesia," Copyright © J.H.M. van Oostrom, 1993, 131 pages.

* cited by examiner

*Primary Examiner*—Joseph Pelham
(74) *Attorney, Agent, or Firm*—Foley & Lardner; Peter J. Vogel; Michael A. Della Penna (57) ABSTRACT

The invention relates to a system for and a method of establishing monitoring alarm limits based on physiological variables. Such a method can include the steps of receiving a plurality of physiological variable data where the physiological variable data is representative of physiological wellness variables, correlating alarm states of the physiological wellness variables with alarm states of physiological measurable variables, and providing a best clinical selection for the alarm limits.

33 Claims, 8 Drawing Sheets

SYSTEM FOR AND METHOD OF ESTABLISHING MONITORING ALARM LIMITS BASED ON PHYSIOLOGICAL VARIABLES

BACKGROUND OF THE INVENTION

The present invention relates generally to monitoring systems and methods. More particularly, one embodiment of the present invention relates to a system for and method of establishing monitoring alarm limits based on physiological variables.

In general, alarm systems of physiologic monitors support two attributes of clinicians: vigilance and decision making. Of these two attributes, a monitor's alarms are especially needed for vigilance since clinicians, as humans, are relatively poor at this task. An alarm should vigilantly wait for an ominous change in the patient's condition, correctly notifying the clinician of that change. A secondary function of an alarm is to point to the origin of the problem that caused the alarm. Ample research shows that current alarm systems fail in both measures. See, for example, Keenan, R. L. "Anesthetic disasters: incidence, causes, preventability." American Society of Anesthesiologists. *ASA annual refresher course lectures*, 221 (1987): 1–6; Lunn, J. N. and H. B. Devlin. "Lessons from the confidential inquiry into peri-operative deaths in three NHS regions." *Lancet* 2 (1987): 1384; Koski, E. M., A. Mäkivirta, T. Sukuvaara and A. Kari. "Clinicians' opinions on alarm limits and urgency of therapeutic responses." *International Journal of Clinical Monitoring and Computing* 12 (1995): 85–88; and Meredith C. and J. Edworthy. "Are there too many alarms in the intensive care unit? An overview of the problems." *Journal of Advanced Nursing* 21.1 (1995): 15–20.

While simple threshold alarm systems currently employed in physiologic monitors are vigilant, these alarms are often spurious. For example, conventional alarms will sound the moment a physiologic variable exceeds the threshold set for it. Although the alarm is reliably triggered when it was instructed to, often there is no justification for the alarm. In one study, researchers surveyed the problems with alarms in intensive care units, citing excessive false alarms among other problems. Meredith C. and J. Edworthy. "Are there too many alarms in the intensive care unit? An overview of the problems." *Journal of Advanced Nursing* 21.1 (1995): 15–20.

In a survey of alarms at a children's hospital intensive care unit (ICU), researchers found after 298 monitored hrs, 86% of a total 2,942 alarms were found to be false-positive alarms, while an additional 6% were classified as clinically irrelevant true alarms. See, Tsien, C. L. and J. C. Fackler. "Poor prognosis for existing monitors in the intensive care unit." *Critical Care Medicine* 25 (1997): 614–619. Only 8% of all alarms tracked during the study period were determined to be true alarms with clinical significance.

A study of alarms in the anesthesia environment showed 40–75% of alarms in the anesthesia environment are false. See, Mylrea, R. A., J. A. Orr and D. R. Westenskow. "Integration of monitoring for intelligent alarm in anesthesia: neural networks—can they help." *Journal of Clinical Monitoring* 9 (1993): 31–37. From another perspective, other researchers found that only 7% of anesthesia-based alarms turned out to be useful. Meijler, A. P. "Automation in anesthesia—a relief?" Berlin: Sprinter-Verlag, 1987. In a survey of 852 anesthesiologists, researchers determined that 58% of respondents had disabled all alarms at the beginning of a case and that 25% did so routinely. See, McIntyre, J. W. "Ergonomics: Anaesthetists' use of auditory alarms in the operating room." *International Journal of Clinical Monitoring and Computing* 2 (1985): 47–55.

Conventional alarm systems of physiologic monitors are weak because they exhibit a high false positive rate and when alarms are true positives they are often clinically irrelevant. Alarm limits used in such conventional alarm systems are based generally on only clinical experience and/or approximations. Such alarm limit approximations are often overly inclusive, resulting in high incidents of false positive or clinically irrelevant alarms. Whatever improvements to an alarm system are made, clinicians must be able to use them on patients on a day-to-day basis in a way that improves patient care.

Thus, there is a need for an alarm system for physiologic monitors which provide more accurate alerts. Further, there is a need for an accurate alarm system for physiologic monitors which is commercially viable. Even further, there is a need for determining more appropriate alarm limits for a physiologic monitor, resulting in more meaningful alarms.

The teachings hereinbelow extend to those embodiments which fall within the scope of the appended claims, regardless of whether they accomplish one or more of the above-mentioned needs.

SUMMARY OF THE INVENTION

The present invention relates to a method and system for establishing monitoring alarm conditions based on system variables. This system or method can include receiving a plurality of system variable data where the system variable data is representative of system acceptability variables, correlating alarm states of the system acceptability variables with alarm states of the system measurable variables, and providing a best clinical selection for the alarm limits.

One exemplary embodiment of the invention is related to a method of establishing monitoring alarm limits based on physiological variables. This method can include the steps of receiving a plurality of physiological variable data where the physiological variable data is representative of physiological wellness variables, correlating alarm states of the physiological wellness variables with alarm states of the physiological measurable variables, and providing a best clinical selection for the alarm limits.

Another exemplary embodiment of the invention is related to a computer implemented method of establishing alarm limits for a physiological monitor. The physiological monitor is configured to monitor measurable variables of a patient. This method can include associating alarm states of wellness physiological variables with measurable physiological variables, providing a range of acceptable alarm limits based on the associated alarm states, and selecting monitor alarm limits for a physiological monitor based on the provided range of acceptable alarm limits.

Another exemplary embodiment of the invention is related to a system for establishing monitoring physiological alarm limits based on calculated physiological variables. This system can include means for receiving a plurality of physiological variable data where the physiological variable data is representative of physiological wellness variables, means for correlating alarm states of the wellness physiological wellness variables with physiological measurable variables, and means for providing a best clinical selection for the alarm limits.

Another exemplary embodiment of the invention relates to a method of establishing monitoring alarm limits based on system variables. This method can include the steps of receiving a plurality of system variable data where the system variable data is representative of system acceptability variables, correlating alarm states of the system acceptability variables with alarm states of system measurable variables; and providing a manufacture determined selection for the alarm limits.

Another exemplary embodiment of the invention relates to a computer implemented method of establishing alarm limits for a monitor where the monitor is configured to monitor measurable variables of a system. This method can include associating alarm states of system acceptability variables with alarm states of system measurable variables, providing a range of acceptable alarm limits based on the associated alarm states, and selecting monitor alarm limits for a monitor based on the provided range of acceptable alarm limits.

Other principle features and advantages of the invention will become apparent to those skilled in the art upon review of the following drawings, the detailed description, and the appended claims.

BRIEF DESCRIPTION OF THE DRAWINGS

The exemplary embodiments will hereafter be described with reference to the accompanying drawings, wherein like numerals denote like elements, and.

DETAILED DESCRIPTION OF THE EXEMPLARY EMBODIMENTS

A system for and method of setting monitoring alarm limits based on physiological variables are described. In the following description, for purposes of explanation, numerous specific details are set forth in order to provide a thorough understanding of the present invention. It will be evident, however, to one skilled in the art that the exemplary embodiments may be practiced without these specific details. In other instances, well-known structures and devices are shown in block diagram form in order to facilitate description of the exemplary embodiments.

In one embodiment, a computer system is used which has a central processing unit (CPU) that executes sequences of instructions contained in a memory. More specifically, execution of the sequences of instructions causes the CPU to perform steps, which are described below. The instructions may be loaded into a random access memory (RAM) for execution by the CPU from a read-only memory (ROM), a mass storage device, or some other persistent storage. In other embodiments, hardwired circuitry may be used in place of, or in combination with, software instructions to implement the functions described. Thus, the embodiments described herein are not limited to any specific combination of hardware circuitry and software, nor to any particular source for the instructions executed by the computer system.

Figure 1:
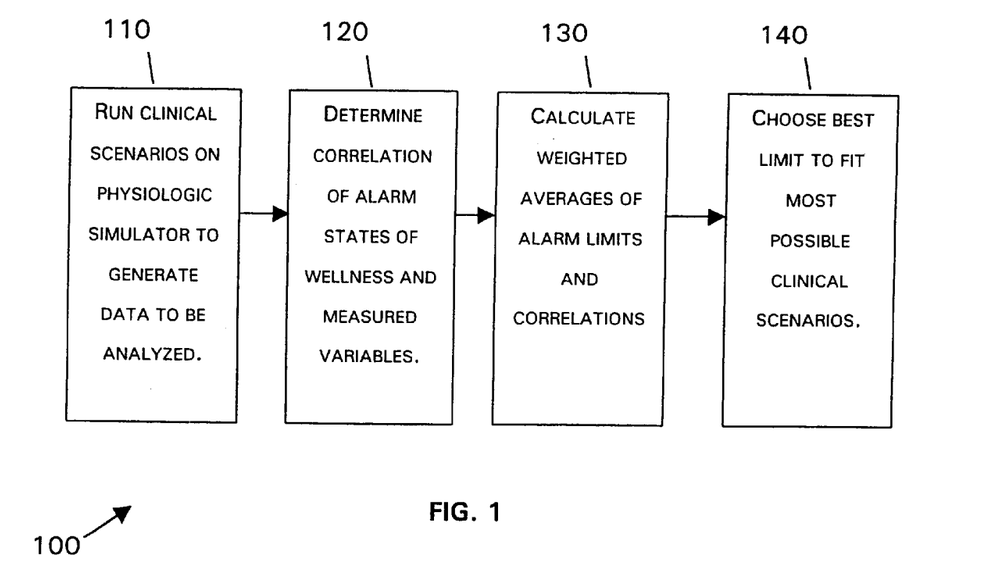
FIG. 1 is a flow diagram illustrating an exemplary method of calculating monitoring alarm limits based on physiological variables.

FIGS. 1–8 are used in the description of an exemplary system and method which produce a more useful, clinically meaningful set of alarm limits for a physiologic monitor. Referring now to FIG. 1, a flow diagram 100 illustrates exemplary steps in a method of setting monitoring alarm limits based on physiological variables. In an exemplary embodiment, a step 110 is performed in which a physiologic model is used to generate a set of data to analyze. A model or simulator of the physiologic processes can be used to properly mimic human physiology to be a substitute for a set of real patients. The physiologic processes can be analyzed using a physiologic simulator, such as, the BODY Simulator from Advanced Simulation of Point Roberts, Wash. The physiologic model is based on established principles of transport phenomena and pressure, flow, compliance, and resistance. Such physiologic models have been applied to make working cardiovascular and respiratory systems that transport oxygen, drugs, and carbon dioxide, for instance.

As an example, the simulator can model the cardiovascular and pulmonary systems along with an uptake and distribution model for inhaled anesthetics and other medications. The simulator provides feedback between the cardiovascular and pulmonary models such that medication concentration in various compartments of the cardiovascular model affects the contractility of the heart, changing the uptake and distribution of the medication. Similarly, medication concentration affects the $CO_2$ modulation of myocardial contractility, and the baroreceptor-heart rate control loop, which in turn affects the uptake and distribution of medication. The simulator can be implemented on a hybrid analog/digital computer or completely on a digital computer.

In an exemplary embodiment, the simulator can generate a matrices of numbers or data on wellness variables of the physiological model. Such data can be stored in a computer readable medium, such as, a magnetic or optical disk in a computer readable file containing, for example, ASCII text formatted data. Wellness data can include information from multiple models under a variety of conditions.

In a step 120, alarm states of wellness and measured variables are correlated based on wellness variable information obtained from the simulator. In an exemplary embodiment, such data is communicated from a file in a computer readable medium. The file can be created by the simulator described with reference to step 110. This correlation step associates physiologic variables for which alarm limits are determined (called measurable physiologic variables) with physiologic variables that are better measures of the actual state of the patient (called wellness physiologic variables). Measurable physiologic variables are more readily measurable than wellness physiologic variables.

Given that there are accepted clinical limits for wellness physiologic variables, limits for the measurable variables can be determined by correlation with the wellness physiologic variables. Exemplary techniques for correlating wellness and measurable variables are described below with respect to FIGS. 2–6.

After step 120, a step 130 is performed in which the results of many clinical scenarios from the simulator are combined through a weighted average scheme utilizing the strength of the correlation with the optimum alarm limit for each scenario evaluated. Exemplary techniques for weight averaging the correlation are described below with reference to FIGS. 7–8.

After step 130, a step 140 is performed in which a best clinical alarm limit is established. In an exemplary embodiment, the optimum alarm limits for measurable variables are established by relating them to wellness variables calculated by mathematical models. For example, a physiologic model can be driven towards a negative clinical outcome such as oxygen deprivation. A time sequence of alarms for both wellness and measured variables can then be generated. A set of limits for the measured variables is then based on a set of limits for the wellness variables. Mathematically, this relationship can be described as:

$$\text{Limits}_{measured}[A^n] = f(\text{Limits}_{wellness}[B^k])$$

where

A=n-dimension vector of alarm limits of measured variables

B=k-dimension vector of alarm limits of wellness variables.

The physiologic variables, both wellness and measurable, are considered in terms of their alarm status. An alarm limit of a measurable variable can be determined relative to a known limit of a wellness variable. The limit of the wellness variable is fixed, based on the level at which injury occurs as reported in the literature. The limit of the measurable variable is then varied over all possible values until a best correlation occurs between the measured variable alarm status and the wellness variable alarm status.

Figure 2:
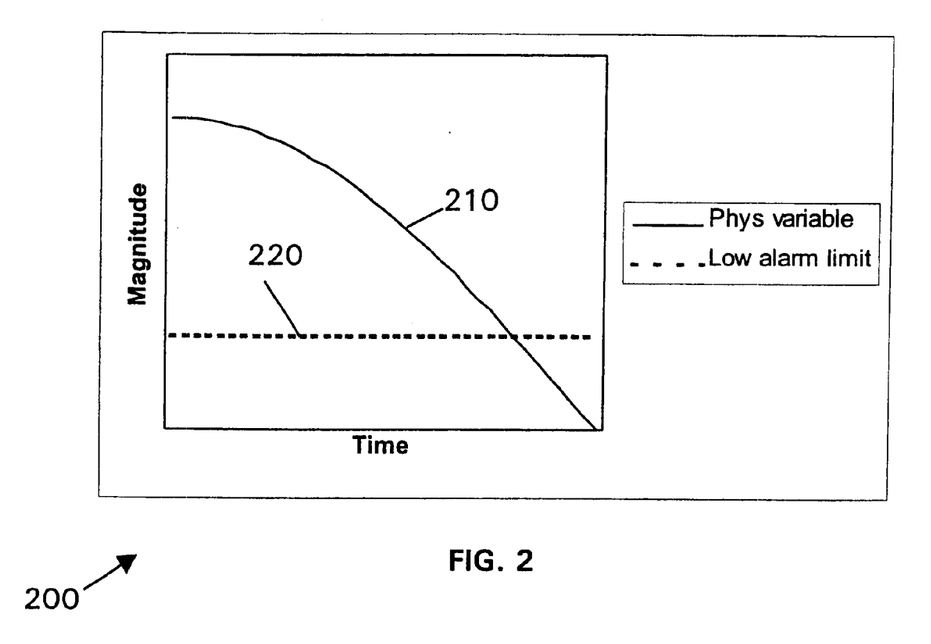
FIG. 2 is a graph of an exemplary physiological variable over time.

Graphically, this transformation from wellness to measurable variables can be shown as follows. In FIG. 2, a graph 200 illustrates a line 210 depicting the magnitude of an arbitrary continuous physiologic variable over time. A line 220 in graph 200 indicates a low alarm limit corresponding to the physiologic variable represented by line 210. An alarm status of this variable can be generated by transforming the continuous variable to a binary variable.

Figure 3:
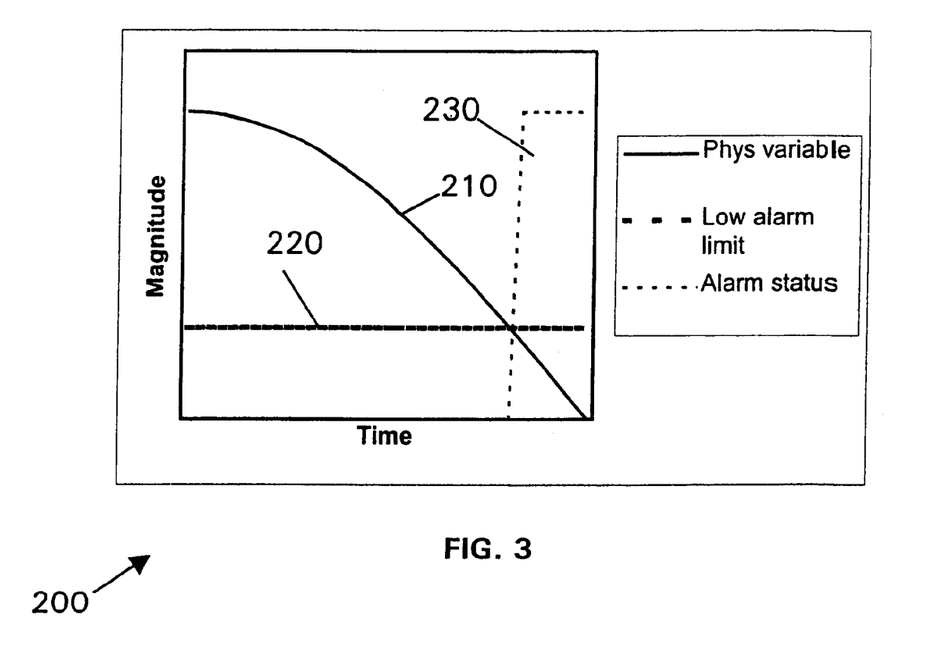
FIG. 3 is a graph of an exemplary physiological variable over time and an alarm status of the physiologic variable.

FIG. 3 illustrates graph 200 having an alarm status indication 230 which achieves a non-zero value once line 210 drops below low alarm limit line 220. It can be seen that as the alarm level moves down (in this instance), the onset of the alarm moves later in time. Of course, for a different physiologic variable curve, a completely different family of alarm status curves can result. Note also that an alarm limit can be applied to a non-monotonically decreasing function, resulting in an alarm status that alters between periods of On and Off as the function passed through the alarm limit.

Figure 4:
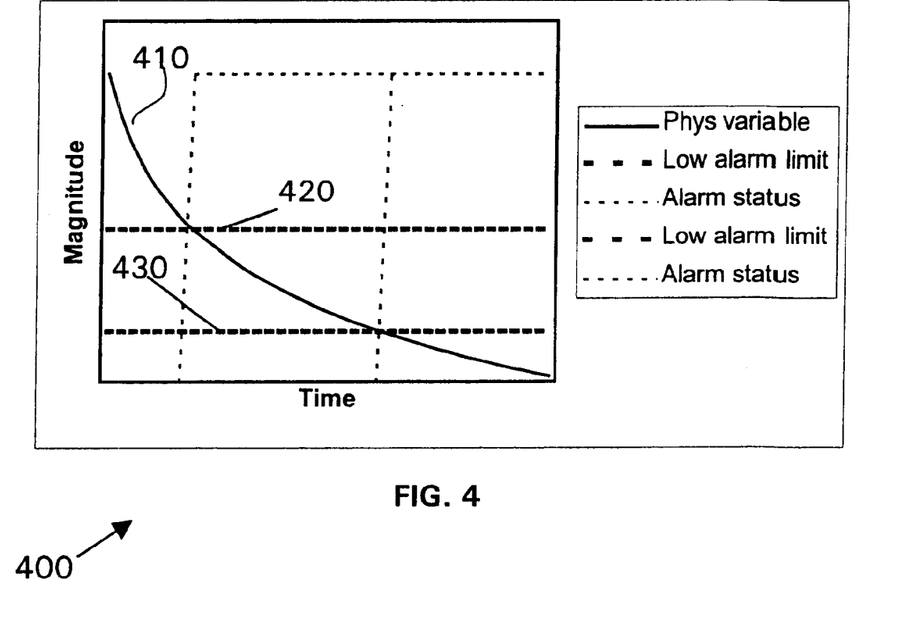
FIG. 4 is a graph of an exemplary physiological variable over time and two alarm statuses of the physiologic variable.
Figure 5:
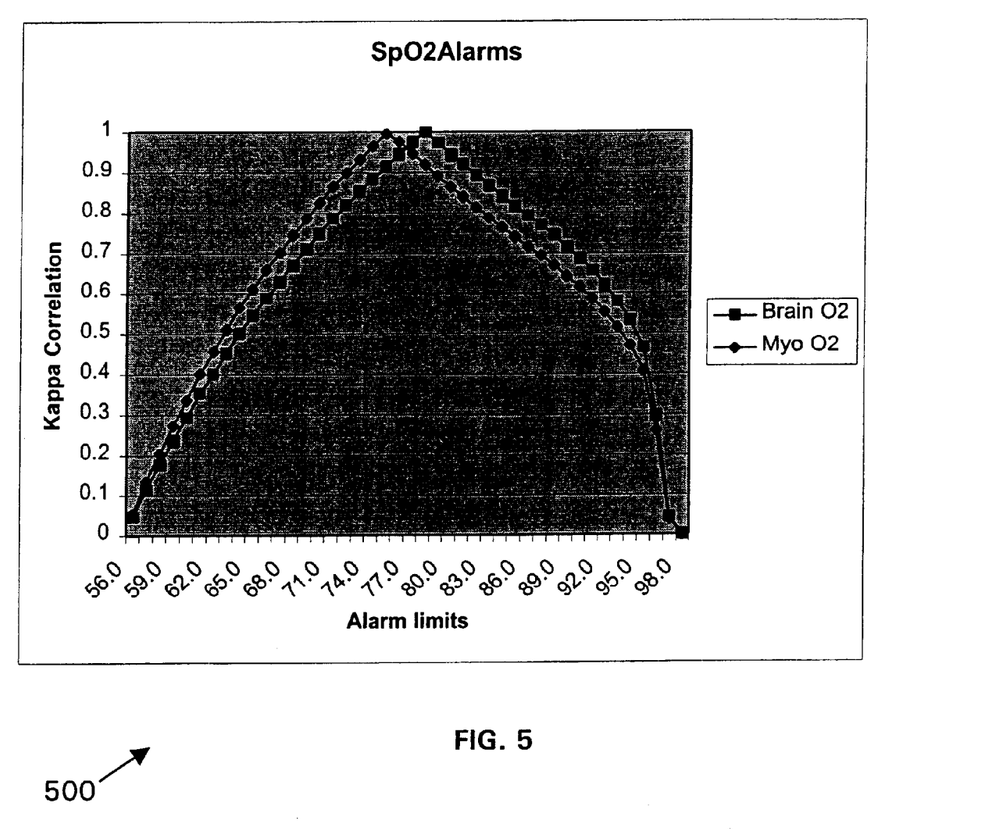
FIG. 5 is a graph illustrating a Kappa correlation between the alarm state of a measured physiologic variable over a range of possible alarm limits and the alarm state of two wellness variables.
Figure 6:
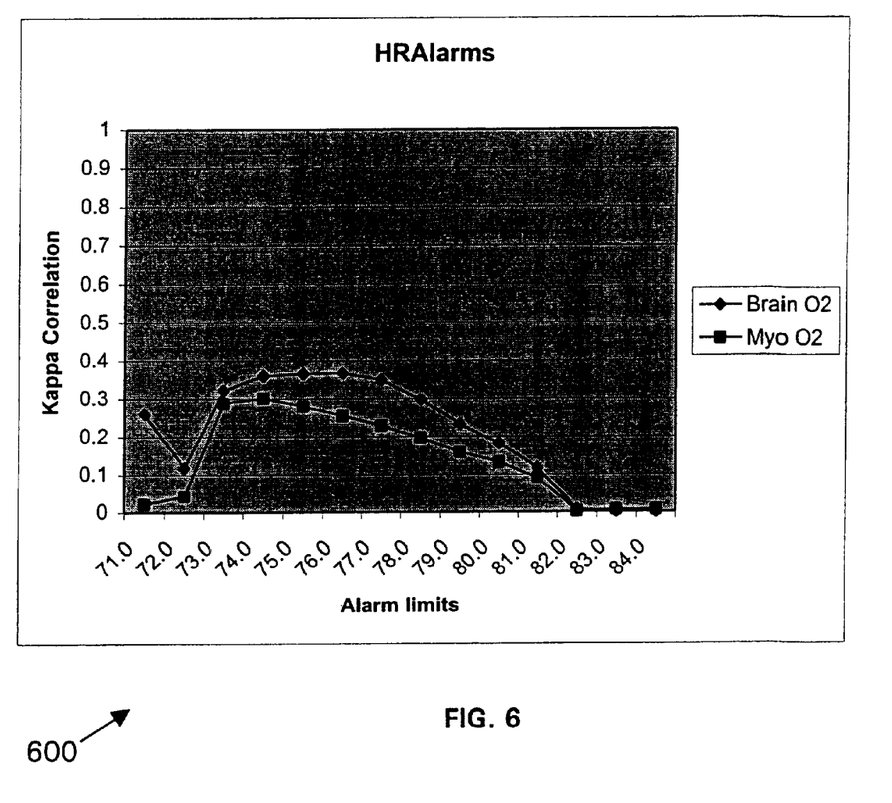
FIG. 6 is a graph illustrating a Kappa correlation between the alarm state of a measured physiologic variable over a range of possible alarm limits and the alarm state of two wellness variables.

FIG. 4 illustrates a graph 400 depicting a line 410 showing the magnitude of a second physiologic variable over time. A line 420 indicates a first low alarm limit and a line 430 represents a second low alarm limit. Using multiple physiologic variables, a family of binary variables can be created.

Following this example, the process described with reference to FIGS. 1–8 then determines best low alarm limit to select for the second physiologic variable (FIG. 4) to match the alarm status of the first physiologic variable (FIG. 3). Given the finite range of a physiologic variable, it is possible to examine all possible values of an alarm limit. For example, a heart rate will only reasonably vary between 0 and 250; arterial oxygen saturation can only exist between 0 and 100%. In an exemplary embodiment, a range that a variable traverses within a data set can be considered. For instance, it may be that the heart rate during a trial will be between 40 and 180 or the arterial oxygen saturation between 40 and 100%.

In examining these values, a mechanism is used to determine the best match between the two sets of alarm status curves, one being from the first physiologic variable and the second being alarm status curve under test of the second physiologic variable. In an exemplary embodiment, a Kappa statistic is used to analyze the agreement between two ordinal or nominal variables. While a Pearson's r statistic could be calculated for the alarm status data, a Pearson's r would be inappropriate since it is not a continuous variable. Another possible approach is to calculate the percentage of agreement between the two alarm status variables. Such a calculation is prone to a strong bias error as the vast majority of time there are no alarms present. Advantageously, the Kappa statistic determines the agreement between variables while correcting for a chance agreement.

The calculation for the Kappa statistic is applied to all possible alarm limits, generating a set of correlations for each alarm limit. Plotting corrected agreement against alarm limits can indicate the alarm limit for which there is the best agreement between the alarm statuses of two physiologic variables. An example of plotted alarm limits is shown in graph 500 of FIG. 5.

It is also possible that a measured variable does not have any alarm limit that shows a strong correlation with any wellness variable. In this instance, it would be reasonable to place a much lower priority on this variable when monitoring. An example of this situation is shown graphically by a graph 600 in FIG. 6.

Figure 7:
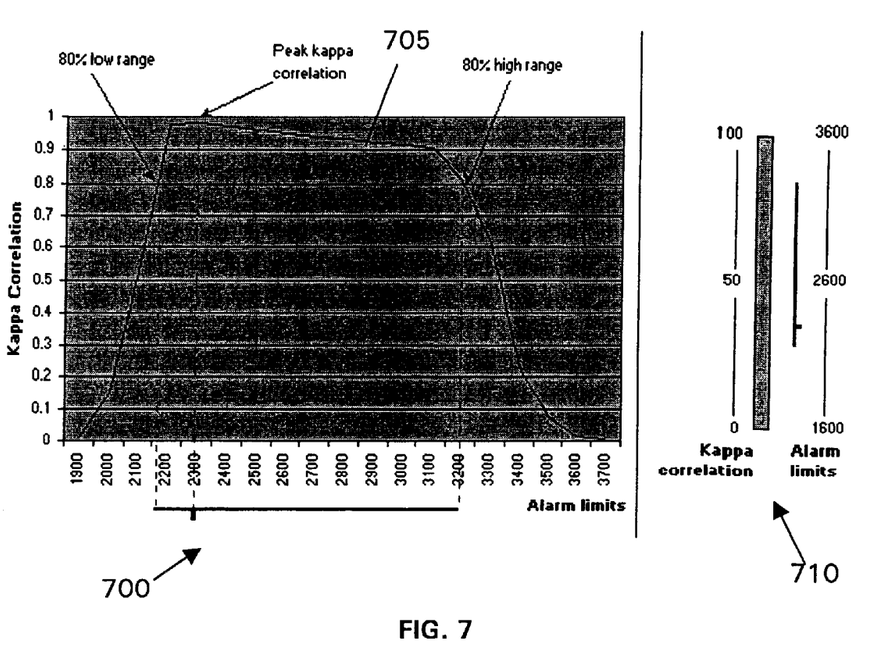
FIG. 7 is a graph illustrating a Kappa correlation curve and a corresponding bar graph representing the alarm limits for the range of 80% of peak correlation.

FIG. 7 illustrates a graph 700 with a Kappa correlation curve 705. A transformation in the peak and 80% range can be made into a one-dimensional graph 710. For each measured variable, the alarm limit ($L_{scenario}$) corresponding with the peak agreement (i.e., maximum kappa) to both wellness variables, the range of alarm limits that corresponds with an agreement of 80% of the peak ($L_{scenario\ 80}$), and the maximum Kappa value can be determined. Such a Kappa value determination can be done for all patient and scenario combinations tested. In addition, a weighted average of the peak alarm limits can be calculated across all test situations and for both wellness variables. The maximum Kappa value provides the weighting to derive a single alarm limit value for a variable that corresponds with the best overall response. One reason for the weighting is to value the alarm limit that is associated with a good correlation to the wellness variable over an alarm limit with poor correlation. For example, if in one test situation, an alarm limit of 50 mmHg results in a kappa statistic of 0.96 and in another situation the best correlation is 0.45 for an alarm limit of 35 mmHg, the limit of 50 should count more towards the overall limit. The weighted average for a measured variable's optimum limit is calculated as where $L_{variable}$ (e.g., $L_{spO2}$) is the optimum alarm limit. Mathematically, the relationship can be represented as:

$$L_{variable} = \frac{\sum_{i=1}^{n} L_i \times kappa_i}{\sum_{i=1}^{n} kappa_i}$$

for all test situations, $L_i$ is the optimum alarm limit for a single test situation, $kappa_i$ is the kappa agreement for a single test situation and i is the particular test situation.

The reporting of the alarm limit range corresponding to 80% of peak agreement is done for at least two reasons. First, since the weighted average limit for a variable ($L_{variable}$) is likely to be different than the weighted average limit ($L_{scenario}$) for any given test situation, it gives us an indication of the impact on the agreement to a wellness variable in a particular situation. For instance, assume that the weighted average calculated for mean arterial pressure is 55 mmHg but for a given patient and clinical scenario the best alarm limit is 47 mmHg. Looking at the 80% range and seeing that it goes from 46 to 56 mmHg, using an alarm limit of 55 mmHg for this patient and situation provides a reasonable alarm response.

Another benefit in reporting the $L_{scenario\ 80}$ ranges is to give a numerical and graphical representation of the "broadness" of the Kappa agreement curve. A curve with a sharp spike indicates that a particular alarm limit is much better than other alarm limits. A broad curve indicates that that particular variable has a wide range of values that would provide a good alarm response. For instance, consider the difference between the heart alarms (described with reference to FIG. 6) and the $SpO_2$ alarms (described with reference to FIG. 5). The heart rate curve is broad, indicating many alarm limits that would provide a reasonable alarm response. On the other hand, the $SpO_2$ curves have a definite peak indicating that one alarm value is better than the others.

Figure 8:
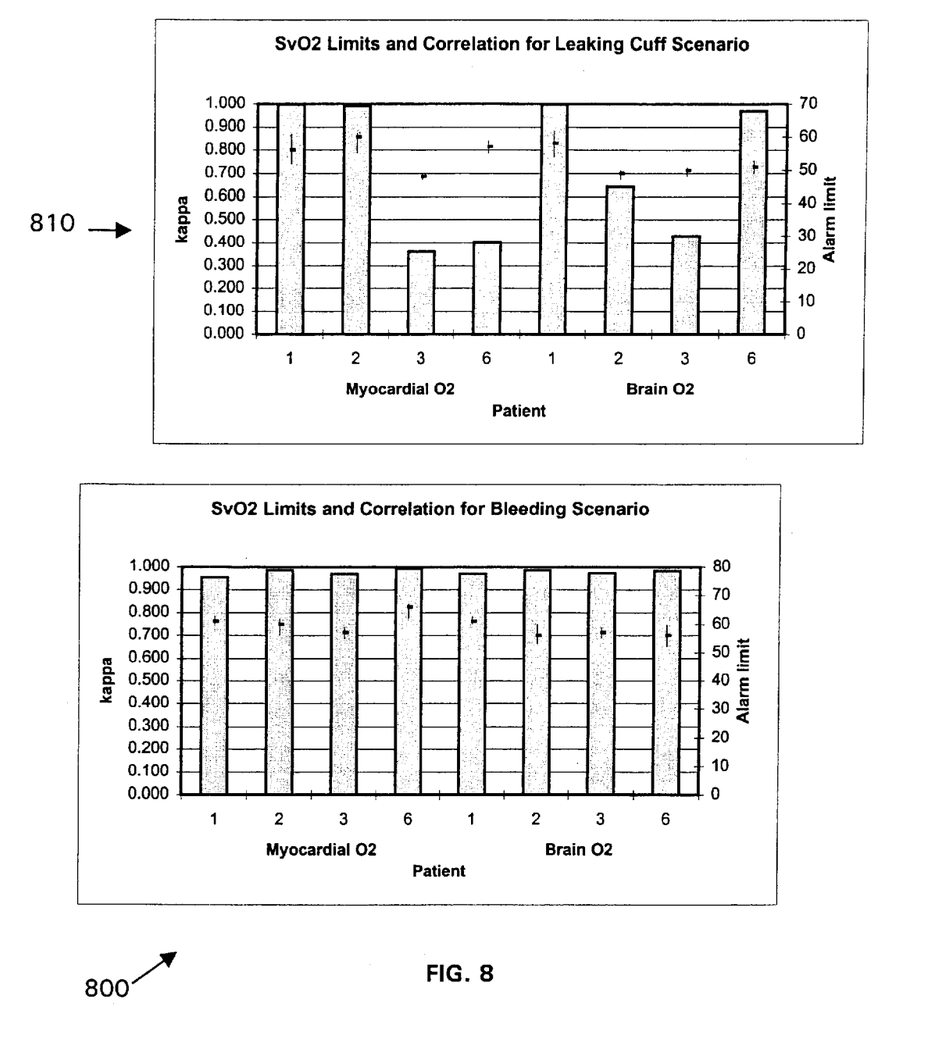
FIG. 8 is a graph illustrating Kappa correlation bar graphs for a range of clinical scenarios and patients.

FIG. 8 illustrates a graph 800 and a graph 810 in which all test scenarios (patient and clinical situations) are combined for a single measured variable. There is a good match between the weighted averages for the bleeding and leaking cuff scenarios. In addition, inspecting graphs 800 and 810, one can see an overlap of most 80% ranges except for Patient 3, who has $L_{scenario}$ that is slightly lower than the other patients for the leaking cuff scenario. Inspecting the trends of the variables for this patient, the reason for this becomes apparent. The patient has a lower cardiac output and therefore a lower oxygen delivery. After the tissues consume the oxygen they require, there is less left over in the venous blood.

Since the response from both scenarios is similar, it makes sense to combine these values of 55% and 59% into a single value, 57%. This value passes through nine of the sixteen 80% ranges representing all of the scenarios, wellness variables and patients.

Advantageously, the technique described with reference to FIGS. 1–8 is a computationally simple yet powerful method of determining more appropriate alarm limits for a physiologic monitor. More appropriate alarm limits can result in more meaningful alarms because there are fewer false positives. Moreover, with the alarm system indicating actual problems, clinicians rely on the alarms more and are less likely to disable the alarm systems. As such, clinicians are more informed and there is better care for the patient. Further, physiologic monitors containing such alarms are preferred in the marketplace because of the extreme dissatisfaction with current alarm systems.

One advantage to the exemplary system and method of linking wellness variables to measured variables described with reference to FIGS. 1–8 is the ability to refine the linking as new variables are added to simulators (e.g., pH, temperature, etc.) or as clinical research describes the critical levels of wellness variables better. Further, the exemplary technique can be useful as a direct measurement of wellness variables. For example, measuring brain oxygen concentration with conventional systems requires placing a sensor directly in the brain tissue via a bolt in the skull. Further, measuring myocardial oxygen concentration is possible but requires a specialized magnetic resonance system.

Advantageously, the system and method described with reference to FIGS. 1–8 allows measurement of wellness variables, such as, brain oxygen concentration by monitoring a measurable physiologic variable, such as, blood pressure which has a correlation to the wellness variable. As such, a meaningful alarm limit can be established for a wellness variable (e.g., brain oxygen concentration) based on a measurable variable (e.g., blood pressure) without the need for a costly or invasive procedure.

As appreciated by a person of skill in the art, the exemplary systems and methods described herein with reference to FIGS. 1–8 can be embodied in systems or applications other than those used with physiological monitors. For example, alternative embodiments can be utilized in manufacturing systems, such as, drug and chemical manufacturing systems and other systems where monitoring is necessary or desired. In such systems, system measurable variables are used in establishing alarm selections for system acceptability variables associated with a system.

While the exemplary embodiments illustrated in the figures and described above are presently preferred, it should be understood that these embodiments are offered by way of example only. Other embodiments may include, for example, other correlation and averaging techniques. The invention is not limited to a particular embodiment, but extends to various modifications, combinations, and permutations that nevertheless fall within the scope and spirit of the appended claims.

What is claimed is:

1. A method of establishing monitoring alarm limits based on physiologic variables, the method comprising the steps of:
   receiving a plurality of physiological variable data, the physiological variable data being representative of physiological wellness variables;
   correlating alarm states of the physiological wellness variables with alarm states of physiological measurable variables; and
   providing a best clinical selection for the alarm limits.

2. The method of claim 1, wherein the step of receiving a plurality of physiological variable data comprises communicating the physiological variable data from a computer storage medium containing matrices of numbers to a computing device.

3. The method of claim 1, wherein the physiological wellness variables comprise indications of a patient condition which are not easily measurable but can be calculated via models and the physiological measurable variables comprise indications of a patient condition which are more easily measurable.

4. The method of claim 1, wherein the step of correlating alarm states of the physiological wellness variables with alarm states of physiological measurable variables comprises establishing a set of limits for the physiological measurable variables based on a set of limits for the physiological wellness variables.

5. The method of claim 1, wherein the step of correlating alarm states of the physiological wellness variables with alarm states of physiological measurable variables comprises utilizing a Kappa statistic to determine agreement between the alarm states of physiological wellness variables and the alarm states of physiological measurable variables.

6. The method of claim 1, further comprising providing a weighted average of alarm limits and the correlated alarm states.

7. The method of claim 6, wherein the step of providing a weighted average of alarm limits and the correlated alarm states comprises utilizing the formula:

$$L_{variable} = \frac{\sum_{i=1}^{n} L_i \times kappa_i}{\sum_{i=1}^{n} kappa_i}$$

where $L_{variable}$ is the optimum alarm limit for all test situations, $L_i$ is the optimum alarm limit for a single test situation, $kappa_i$ is the kappa agreement for a single test situation and i is the particular test situation and n is a number of scenarios evaluated.

8. A computer implemented method of establishing alarm limits for a physiological monitor, the physiological monitor being configured to monitor measurable variables of a patient, the method comprising:
    associating alarm states of wellness physiological variables with alarm states of measurable physiological variables;
    providing a range of acceptable alarm limits based on the associated alarm states; and
    selecting monitor alarm limits for a physiological monitor based on the provided range of acceptable alarm limits.

9. The computer implemented method of claim 8, wherein the step of associating alarm states of wellness physiological variables with measurable physiological variables comprises statistically comparing alarm limits for the wellness physiological variables with alarm limits for the measurable physiological variables.

10. The computer implemented method of claim 9, wherein the step of statistically comparing alarm limits for the wellness physiological variables with alarm limits for the measurable physiological variables comprises analyzing agreement between the wellness physiological variables and the measurable physiological variables with a Kappa statistic.

11. The computer implemented method of claim 8, wherein the step of providing a range of acceptable alarm limits based on the associated alarm states comprises analyzing agreement between alarm status data of wellness physiological variables.

12. The computer implemented method of claim 8, wherein the step of selecting monitor alarm limits for a physiological monitor based on the provided range of acceptable alarm limits comprises for each measurable physiological variable providing an alarm limit corresponding with a peak agreement of wellness physiological variables.

13. The computer implemented method of claim 12, wherein the range of alarm limits corresponds to an agreement of 80 percent of peak agreement of wellness physiological wellness variables.

14. A system for establishing monitoring physiological alarm limits based on physiological variables, the system comprising:
    means for receiving a plurality of physiological variable data, the physiological variable data being representative of physiological wellness variables;
    means for correlating alarm states of the wellness physiological wellness variables with alarm states of physiological measurable variables; and
    means for providing a best clinical selection for the alarm limits.

15. The system of claim 14, wherein the means for receiving a plurality of physiological variable data comprises means for communicating the physiological variable data from a computer storage medium containing matrices of numbers to a computing device.

16. The system of claim 14, wherein the wellness physiological wellness variables comprise indications of a patient condition which are not easily measurable and the physiological measurable variables comprise indications of a patient condition which are more easily measurable.

17. The system of claim 14, wherein the means for correlating alarm states of the wellness physiological wellness variables with alarm states of physiological measurable variables comprises means for establishing a set of limits for the physiological measurable variables based on a set of limits for the wellness physiological wellness variables.

18. The system of claim 14, wherein the means for correlating alarm states of the wellness physiological wellness variables with alarm states of physiological measurable variables comprises means for utilizing a Kappa statistic to determine agreement between the wellness physiological wellness variables and the physiological measurable variables.

19. The system of claim 14, further comprising means for providing a weighted average of alarm limits and the correlated alarm states.

20. The system of claim 19, wherein the means for providing a weighted average of alarm limits and the correlated alarm states comprises utilizing the formula:

$$L_{variable} = \frac{\sum_{i=1}^{n} L_i \times kappa_i}{\sum_{i=1}^{n} kappa_i}$$

where $L_{variable}$ is the optimum alarm limit for all test situations, $L_i$ is the optimum alarm limit for a single test situation, $kappa_i$ is the kappa agreement for a single test situation and i is the particular test situation and n is a number of scenarios evaluated.

21. The system of claim 14, wherein one of the physiological wellness variables includes a partial pressure of oxygen in the brain, the partial pressure of oxygen in the brain correlating with a blood pressure physiological measurable variable.

22. A method of establishing monitoring alarm limits based on system variables, the method comprising the steps of:
    receiving a plurality of system variable data, the system variable data being representative of system acceptability variables;
    correlating alarm states of the system acceptability variables with alarm states of system measurable variables; and
    providing a manufacture determined selection for the alarm limits.

23. The method of claim 22, wherein the step of receiving a plurality of system variable data comprises communicating the system variable data from a computer storage medium containing matrices of numbers to a computing device.

24. The method of claim 22, wherein the system acceptability variables comprise indications of a system condition which are not easily measurable but can be calculated via models and the system measurable variables comprise indications of a system condition which are more easily measurable.

25. The method of claim 22, wherein the step of correlating alarm states of the system acceptability variables with alarm states of system measurable variables comprises establishing a set of limits for the system measurable variables based on a set of limits for the system acceptability variables.

26. The method of claim 22, wherein the step of correlating alarm states of the system acceptability variables with alarm states of system measurable variables comprises utilizing a Kappa statistic to determine agreement between the alarm states of system acceptability variables and the alarm states of system measurable variables.

27. The method of claim 22, further comprising providing a weighted average of alarm limits and the correlated alarm states.

28. The method of claim 27, wherein the step of providing a weighted average of alarm limits and the correlated alarm states comprises utilizing the formula:

$$L_{variable} = \frac{\sum_{i=1}^{n} L_i \times kappa_i}{\sum_{i=1}^{n} kappa_i}$$

where $L_{variable}$ is the optimum alarm limit for all test situations, $L_i$ is the optimum alarm limit for a single test situation, $kappa_i$ is the kappa agreement for a single test situation and i is the particular test situation and n is a number of scenarios evaluated.

29. A computer implemented method of establishing alarm limits for a monitor, the monitor being configured to monitor measurable variables of a system, the method comprising:

associating alarm states of system acceptability variables with alarm states of system measurable variables;

providing a range of acceptable alarm limits based on the associated alarm states; and selecting monitor alarm limits for a monitor based on the provided range of acceptable alarm limits.

30. The computer implemented method of claim 29, wherein the step of statistically comparing alarm limits for the system acceptability variables with alarm limits for the system measurable variables comprises analyzing agreement between the system acceptability variables and the system measurable variables with a Kappa statistic.

31. The computer implemented method of claim 29, wherein the step of providing a range of acceptable alarm limits based on the associated alarm states comprises analyzing agreement between alarm status data of system acceptability variables.

32. The computer implemented method of claim 29, wherein the step of selecting monitor alarm limits for a monitor based on the provided range of acceptable alarm limits comprises for each system measurable variable providing an alarm limit corresponding with a peak agreement of system acceptability variables.

33. The computer implemented method of claim 32, wherein the range of alarm limits corresponds to an agreement of 80 percent of peak agreement of system acceptability variables.

* * * * *